(12) United States Patent
Opel

(10) Patent No.: US 6,325,773 B1
(45) Date of Patent: Dec. 4, 2001

(54) HINGE APPLIANCE FOR MINIMIZING KNEE INJURIES

(76) Inventor: Charles F. Opel, P.O. Box 58423, Houston, TX (US) 77258

( * ) Notice: Subject to any disclaimer, the term of this patent is extended or adjusted under 35 U.S.C. 154(b) by 0 days.

(21) Appl. No.: 09/491,439

(22) Filed: Jan. 26, 2000

Related U.S. Application Data

(60) Provisional application No. 60/139,756, filed on Jun. 17, 1999.

(51) Int. Cl.[7] ................... A61F 5/00; G01L 5/00
(52) U.S. Cl. ................ 602/26; 602/16; 116/203; 116/211
(58) Field of Search ................... 602/5, 20, 23, 602/26, 16; 128/882; 116/203, 211, 212; 16/222; 623/39, 27

(56) References Cited

U.S. PATENT DOCUMENTS

| | | | |
|---|---|---|---|
| 3,799,159 | * 3/1974 | Scott | 602/26 |
| 3,964,299 | * 6/1976 | Johnson | 116/212 |
| 4,655,201 | * 4/1987 | Pirmantgen | 602/26 |
| 4,698,623 | * 10/1987 | Smith | 116/212 |
| 5,323,729 | * 6/1994 | Rubey | 116/203 |
| 5,372,574 | * 12/1994 | Hino et al. | 602/16 |
| 5,421,810 | * 6/1995 | Davis et al. | 602/16 |
| 5,460,599 | * 10/1995 | Davis et al. | 602/26 |
| 5,520,622 | * 5/1996 | Bastyr et al. | 602/16 |
| 5,865,166 | * 2/1999 | Fitzpatrick et al. | 128/117.1 |

* cited by examiner

Primary Examiner—Denise Pothier
(74) Attorney, Agent, or Firm—Kenneth A. Roddy

(57) ABSTRACT

A knee hinge appliance has a pair of hinge assemblies that are secured on the leg of a wearer on opposed lateral sides of the knee joint. Each hinge assembly is formed of juxtaposed first and second disks that rotate relative to one another about a transverse axis extending through the knee joint. The first disk has an upper arm secured to an upper strap or band that encircles the thigh just above the knee joint, and the second disk has a lower arm which is secured to a lower strap or band that encircles the lower leg just below the knee joint. The disks have a cam that slides freely in a circular channel with stop members that allow normal flexing of the knee joint but prevent rotation when the knee is subjected to a blow from the front and prevent excessive lateral movement between the upper and lower leg. A pair of chambers in the disks are filled with a colored liquid which is released upon the disks being subjected to a predetermined lateral force to give a visual indication that the knee joint has received a serious lateral impact and indicates that a replacement hinge assembly is needed.

13 Claims, 5 Drawing Sheets

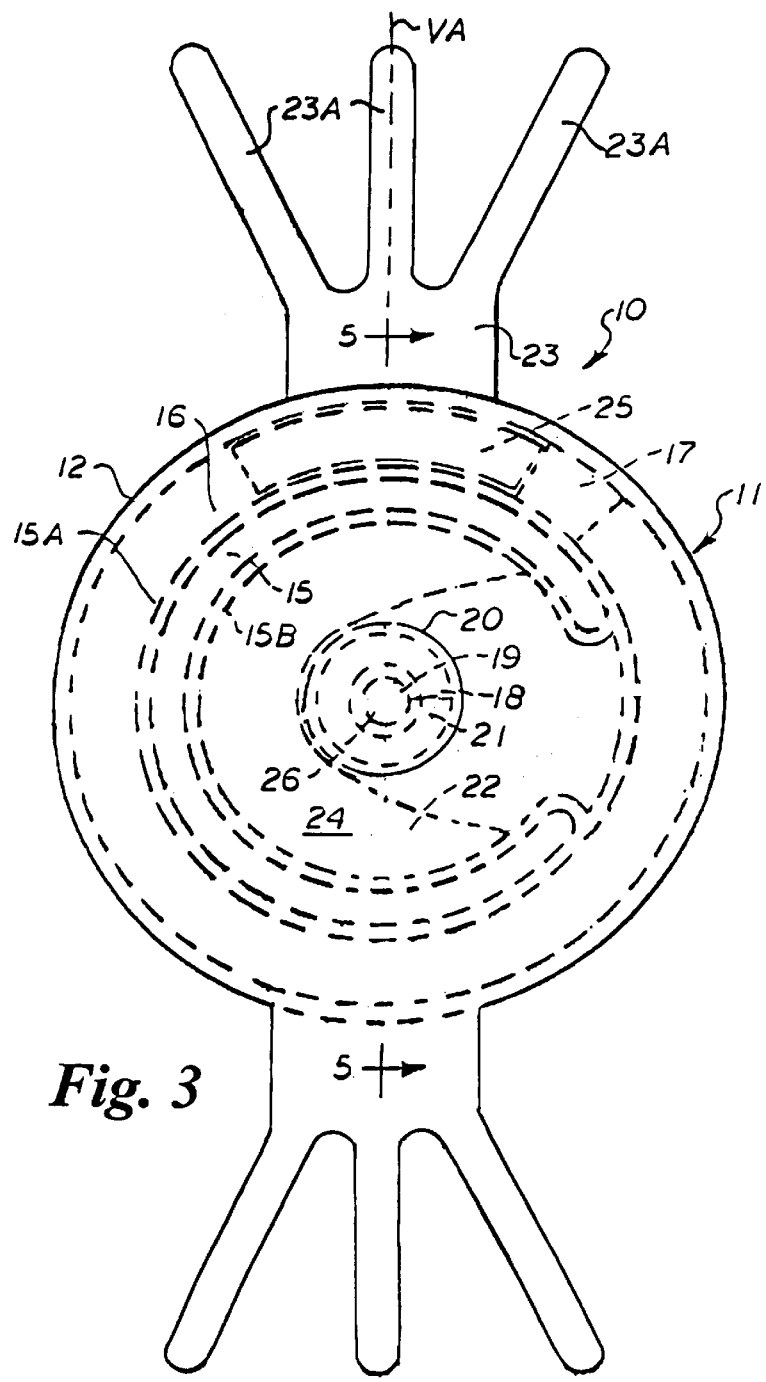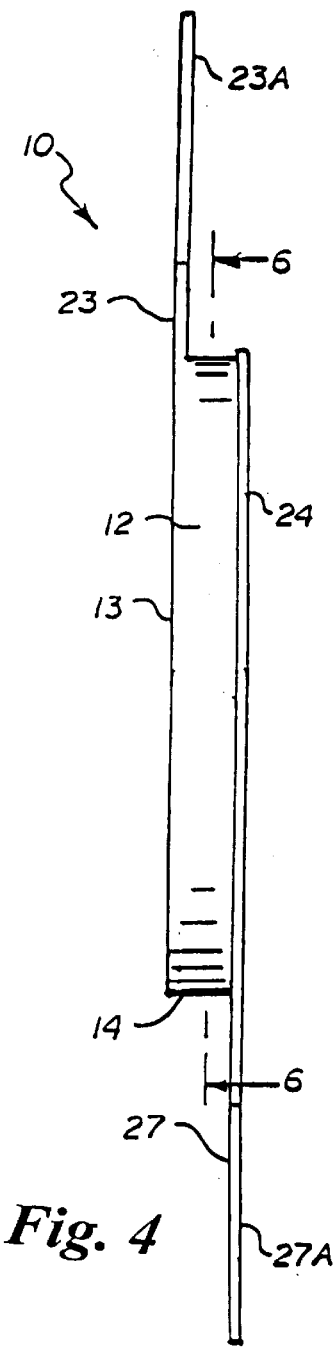
Fig. 3
Fig. 4

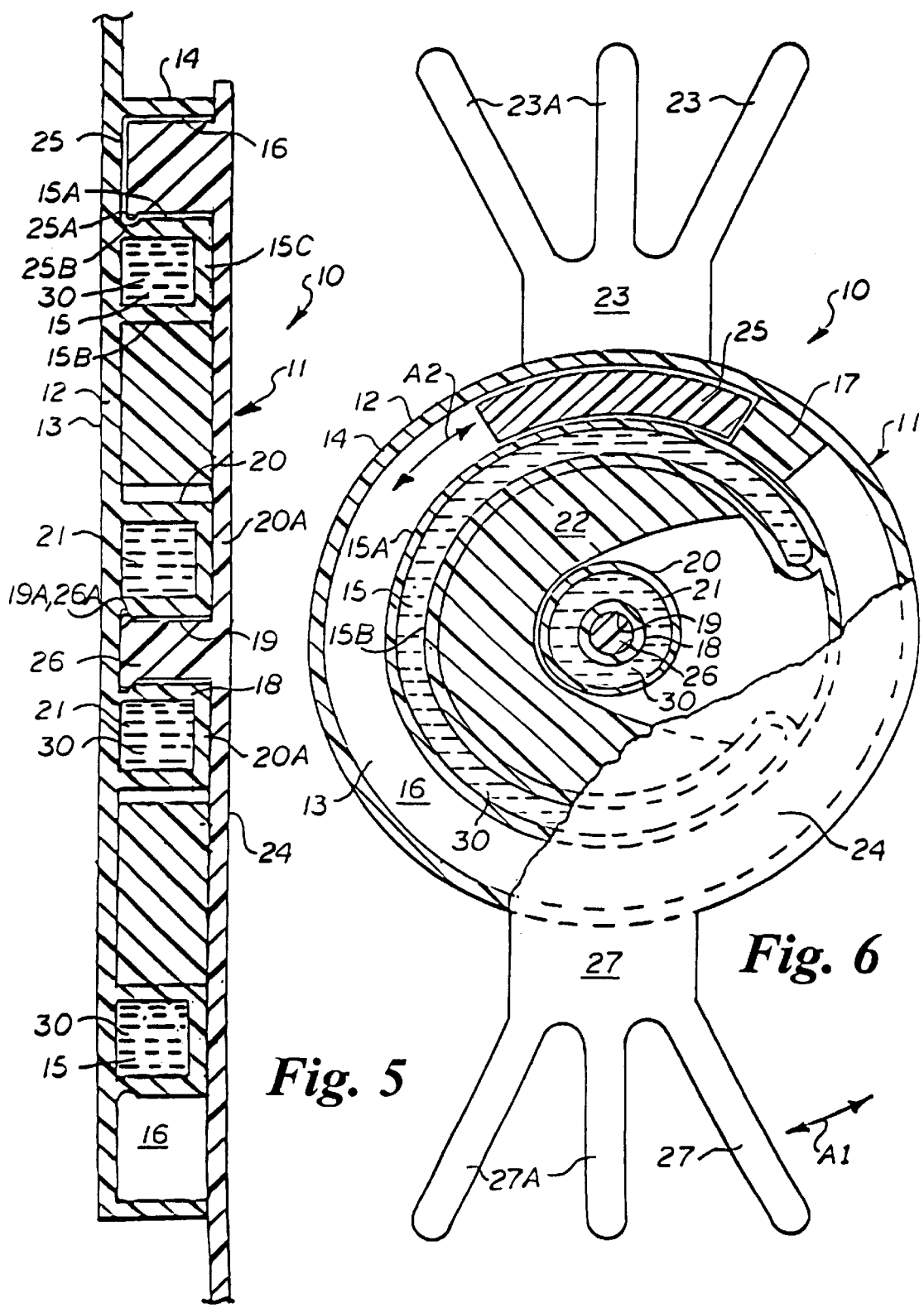

HINGE APPLIANCE FOR MINIMIZING KNEE INJURIES

CROSS REFERENCE TO RELATED APPLICATION

This application claims priority of U.S. Provisional Application Serial No. 60/139,756, filed Jun. 17, 1999.

BACKGROUND OF THE INVENTION

1. Field of the Invention

This invention relates generally to knee braces, and more particularly to a hinge appliance having juxtaposed rotating disks with a cam and stop members that prevent rotation when the knee is subjected to a blow from the front and prevent excessive lateral movement between the upper and lower leg and a pair of chambers in the disks filled with a colored liquid that is released upon the disks being subjected to a predetermined lateral force to give a visual indication that the knee joint has received a serious lateral impact and indicates that a replacement hinge assembly is needed.

2. Brief Description of the Prior Art

Athletes and occasional participants in sporting events and recreational such as baseball, football, basketball, volley ball, tennis, running and cycling has often resulted in debilitating injuries, especially to the knee. Often, the injury requires surgical procedures to repair the joint followed by a program of physical therapy.

There are many patents directed toward knee braces and orthopedic appliances, most of which are bulky and/or complicated heavy metal devices that are worn after an injury to immobilize the joint, to allow only a limited range of motion, or to bear the weight of the wearer during the rehabilitation process.

Townsend, U.S. Pat. No. 4,773,404 discloses a multi-axis controlled motion knee orthosis appliance for controlling an unstable knee joint in the sagittal, coronal and transverse planes, comprising femoral and tibial cuffs joined by links which are interconnected to provide a novel mechanical joint wherein camming slots are formed in one of the links with cams disposed on the other link, the slots comprising straight segments and arcuate segments so as to provide approximately 8 millimeters of sliding movement between the femur and tibia, followed by relative rotation about the center of radius of the femoral condyle as the leg is flexed. The tibial cuff is conformed about the boney prominence or shin of the tibia to inhibit rotation of the leg beneath the knee within the brace itself.

Kausek, U.S. Pat. No. 4,966,133 discloses a knee brace for control of ligament instability in all planes having upper and lower cuffs above and below the knee, a polycentric hinge on the lateral side of the knee, and a medial articulation plate on the medial side of the knee. The cuffs are attached to the leg with non-stretchable straps and provide anterior-posterior stability. The medial pivot plate is designed to stabilize the brace on the medial side of the knee and in conjunction with the lateral hinge and a lateral plate provides medial-lateral stability.

Airy, U.S. Pat. No. 5,052,379 discloses a combination brace and exercise apparatus for body joints that is worn by the user in various configurations, including as a splint to hold a body joint immovable, as a brace to permit the body joint to move through a controlled range of motion and as an exercise apparatus to impart resistance to the flexing and/or extension movement of the body joint. The apparatus includes an articulating frame composed of a first frame section connectable to the first limb of a body joint and a second frame section connectable to a second limb of a body joint. The two frame sections are interconnected together by pivot joint assemblies to permit the frame to articulate about a transverse axis corresponding to the anatomical pivot axis of the body joint. A control plate having adjustable stop pins is mounted on the pivot joint assemblies to control the range of motion of the articulating frame. With the control plate in place, various types of resistance units may be employed to resist relative movement of the frame sections in either or both directions about the pivot axis.

Harris et al, U.S. Pat. No. 5,074,290 discloses a floating pivot hinge and knee brace that includes a thigh cuff having inner and outer spaced brace arms adapted to extend along the user's thigh toward the knee, a calf cuff including inner and outer spaced brace arms adapted to extend along the user's calf toward the knee, and floating pivot axis hinges rotatably connecting the inner and outer brace arms of each pair. The hinge is formed by a pair of juxtaposed hinge plates, each having a pivot face in opposition to a pivot face on the juxtaposed plate, with a concave groove in each of the face. A pivot bearing ball is confined between the opposed faces and retained in the concave grooves. A spring, bellville spring, or disk spring biases the hinge plates together when the pivot bearing ball is positioned in the opposed grooves between. The pivot bearing ball provides a floating pivot axis for hinge rotation of the hinge plates and braces relative to each other, the ball and concave grooves allowing the hinge plates simultaneously to slide and pivot relative to each other.

Gildersleeve, U.S. Pat. No. 5,316,547 discloses an orthopedic brace having one or more pneumatic pads mounted thereon to provide secure and comfort able support for the brace when positioned against the body of a user. Each pad includes at least one pneumatic bladder, formed from a flexible skin permanently sealed to enclose a volume of gas therein.

Most of the devices of the type described above are not suitable for use while participating in strenuous exercise or sports activities to prevent an injury from occurring in the first place, and some could even cause an injury to the wearer or other participant if worn during such activities.

Therefore it would be desirable to provide a lightweight disposable knee hinge appliance that may be worn to prevent injuries to the knee joint that supplements the natural resistance of the joint to excessive movement and will alert the wearer when the joint has received a substantial impact.

The present invention is distinguished over the prior art in general, and these patents in particular by a knee hinge appliance having a pair of hinge assemblies that are secured on the leg of a wearer on opposed lateral sides of the knee joint. Each hinge assembly is formed of juxtaposed first and second disks that rotate relative to one another about a transverse axis extending through the knee joint. The first disk has an upper arm secured to an upper strap or band that encircles the thigh just above the knee joint, and the second disk has a lower arm which is secured to a lower strap or band that encircles the lower leg just below the knee joint. The disks have a cam that slides freely in a circular channel with stop members that allow normal flexing of the knee joint but prevent rotation when the knee is subjected to a blow from the front and prevent excessive lateral movement between the upper and lower leg. A pair of chambers in the disks are filled with a colored liquid which is released upon the disks being subjected to a predetermined lateral force to give a visual indication that the knee joint has received a serious lateral impact and indicates that a replacement hinge assembly is needed.

SUMMARY OF THE INVENTION

It is therefore an object of the present invention to provide a knee hinge appliance to be worn around the knee joint that will minimize the degree and severity of damage to the knee.

It is another object of this invention to provide a knee hinge appliance that allows normal flexing of the knee joint but will prevent rotation when the knee is subjected to a blow from the front.

Another object of this invention is to provide a knee hinge appliance that allows normal flexing and will prevent excessive lateral movement between the upper and lower leg.

Another object of this invention is to provide a knee hinge appliance that will release a colored liquid when the knee joint is subjected to a lateral impact exceeding a predetermined force to give a visual indication that the knee joint has received a serious lateral impact and to indicate that a replacement hinge assembly is needed.

Another object of this invention is to provide a lightweight thin compact knee hinge appliance that may be worn while participating in strenuous exercise or sports activities that will not hinder the natural motion of the knee joint, and will not cause injury to the wearer or other participants if worn during such activities.

A further object of this invention is to provide a knee hinge appliance that has minimum of moving parts, and is rugged and reliable in use.

A still further object of this invention is to provide a knee hinge appliance that is simple in construction, inexpensive to manufacture, and may be disposed of after failure.

Other objects of the invention will become apparent from time to time throughout the specification and claims as hereinafter related.

The above noted objects and other objects of the invention are accomplished by a knee hinge appliance having a pair of hinge assemblies that are secured on the leg of a wearer on opposed lateral sides of the knee joint. Each hinge assembly is formed of juxtaposed first and second disks that rotate relative to one another about a transverse axis extending through the knee joint. The first disk has an upper arm secured to an upper strap or band that encircles the thigh just above the knee joint, and the second disk has a lower arm which is secured to a lower strap or band that encircles the lower leg just below the knee joint. The disks have a cam that slides freely in a circular channel with stop members that allow normal flexing of the knee joint but prevent rotation when the knee is subjected to a blow from the front and prevent excessive lateral movement between the upper and lower leg. A pair of chambers in the disks are filled with a colored liquid which is released upon the disks being subjected to a predetermined lateral force to give a visual indication that the knee joint has received a serious lateral impact and indicates that a replacement hinge assembly is needed.

BRIEF DESCRIPTION OF THE DRAWINGS

FIG. 3 is a plan view showing of the disk members in the assembled condition.

FIG. 4 is a side view of the disk members in the assembled condition.

FIG. 5 is an enlarged longitudinal cross section through the assembled disk members taken along line 5—5 of FIG. 3.

FIG. 6 is a transverse cross section through the assembled disk members showing the direction of rotation of the cam.

DESCRIPTION OF THE PREFERRED EMBODIMENT

Figure 1:
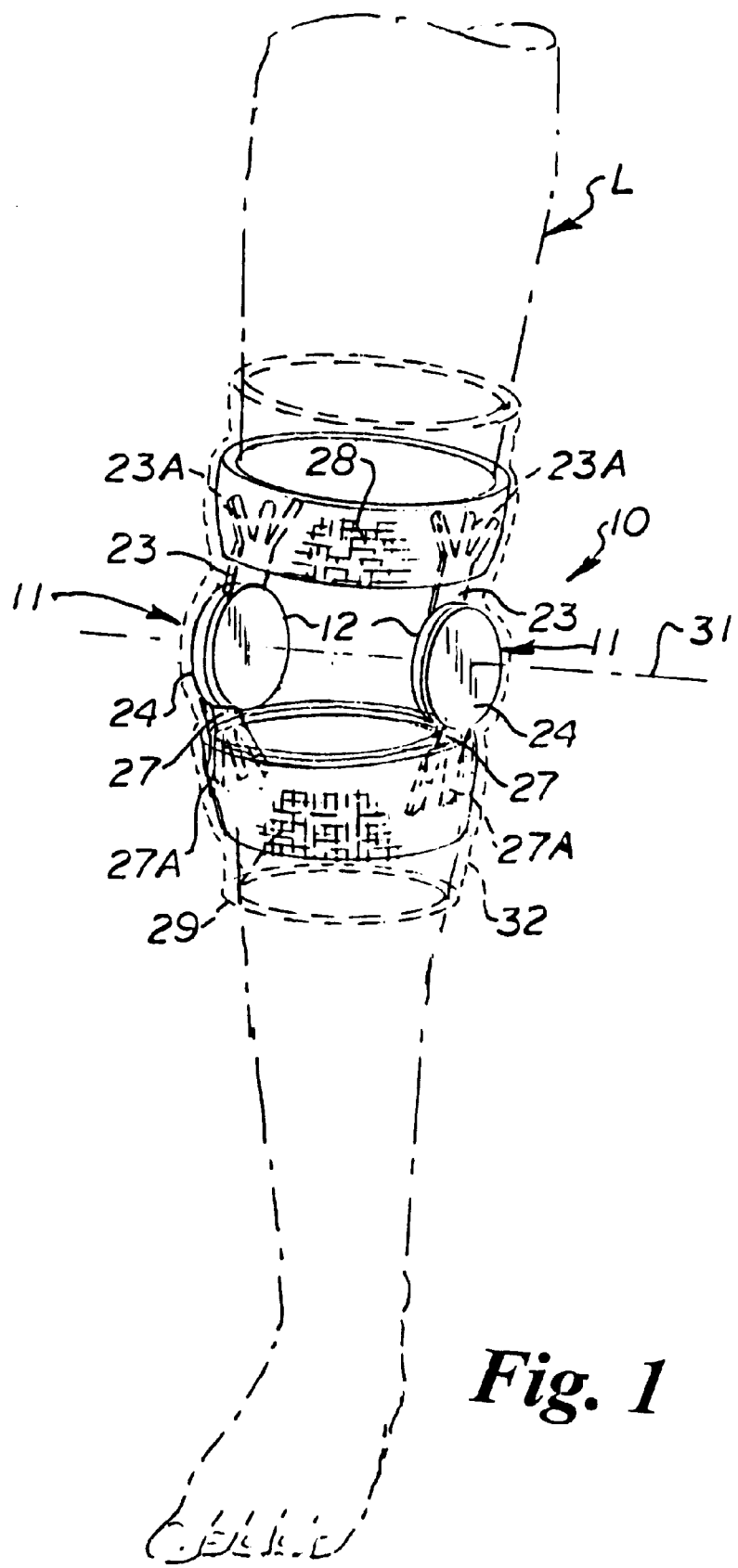
FIG. 1 is an illustration of the hinge appliance in accordance with the present invention secured to the leg of a wearer by a fabric strap or band.

Referring initially to FIG. 1, a pair of knee hinge appliances 10, in accordance with the present invention, are shown secured on the leg L of a wearer on opposed lateral sides of the knee joint. As described in detail hereinafter, each hinge appliance 10 has a hinge assembly 11 formed of juxtaposed first and second disks 12 and 24 that rotate relative to one another about a transverse axis 31 extending through the knee joint. The first disk 12 has an upper arm 23 secured to an upper strap or band 28 that encircles the thigh just above the knee joint, and the second disk 24 has a lower arm 27 which is secured to a lower strap or band 29 that encircles the lower leg just below the knee joint.

As shown in FIGS. 2 through 6, each hinge assembly 11 of the appliance 10 has a first circular disk 12 with a flat end wall 13 and a circumferential side wall 14. A generally C-shaped chamber 15 is spaced radially inward from the circumferential side wall 14 and has a circular outer wall 15A and a concentric inwardly spaced C-shaped inner wall 15B adjoined thereto by a top wall 15C that encloses the chamber. The annulus between the outer wall 15A of the chamber 15 and the circumferential side wall 14 serves as an open guide or circular channel 16 in which an arcuate cam 25 (described below) freely slides. A generally rectangular first stop member 17 is secured in the guide channel 16 in circumferentially offset relation to a vertical axis VA, extending through the center of the upper arm 23 as shown in FIG. 3.

A tubular bushing or hub 18 is disposed in the center of the first disk 12 and has an inwardly extending central bore 19. A circular outer wall 20 encircles the central hub 18 in concentric radially spaced relation and is adjoined thereto by a top wall 20A that forms a second enclosed chamber 21 surrounding the hub. A generally C-shaped second stop member 22 is secured between the outer wall 20 and the inner wall 15B of the chamber 15. A thin flat upper arm 23 extends vertically upward from the circumferential side wall 14 and its outer end is divided into diverging flat fingers 23A.

Each hinge assembly 11 has a second flat circular disk 24 with an arcuate cam 25 protruding from its flat surface. A cylindrical pin 26 protrudes from the center of the flat disk 24 and has a circumferential raised bead 26A at its outer end. A thin flat lower arm 27 extends vertically downward from the outer periphery of the flat disk 24 and its outer end is divided into diverging flat fingers 27A.

As best seen in FIG. 5, the bore 19 of the central hub 18 is provided with a circumferential groove 19A at its bottom end. The first disk 12 and second disk 24 are assembled by placing the pin 26 into the bore 19 and the cam 25 into the guide channel 16 and pressing the disks together until the bead 26A on the pin 26 snaps into sliding engagement with the groove 19A in the hub 18. The lower inner edge of the cam 25 may also be provided with a raised bead 25A that slidably fits into a mating groove 25B at the bottom of the outer wall 15A of the chamber 15. When assembled together, the first and second disks 12 and 24 rotate or pivot relative to one another.

As best seen in FIGS. 5 and 6, the enclosed chambers 15 and 21 are filled with a colored liquid 30, such as water mixed with food coloring, or other suitable colored liquid. This may be accomplished by injecting the liquid into the chambers 15,21 with a syringe or other by other suitable process during the production of the disks.

The disks 12 and 24 are formed of a semi-rigid plastic material. The arms 23 and 27 are sufficiently stiff to support weight in a longitudinal direction and the fingers 23A and 27A are sufficiently thin and flexible so as to wrap around the limb of the wearer, as described below. The wall thickness of the outer wall 15A of the chamber 15 and the wall thickness of the tubular hub 18 that receives the pin 26 are sufficiently thin so as to become distorted upon receiving a sufficient predetermined force and/or may be frangible to break or rupture upon receiving a sufficient predetermined force. The cam 25 and the pin 26 are sufficiently rigid to cause distortion or breakage of the outer wall 15A of the chamber 15 and the wall of the central hub 18, respectively, upon forceful engagement therewith. The stop members 22 and 17 are also sufficiently rigid to stop the travel of the cam 25 and pin 26, as described hereinafter. It should be understood that the various components just described may be formed out of different plastic materials, to achieve the described characteristics.

Figure 2:
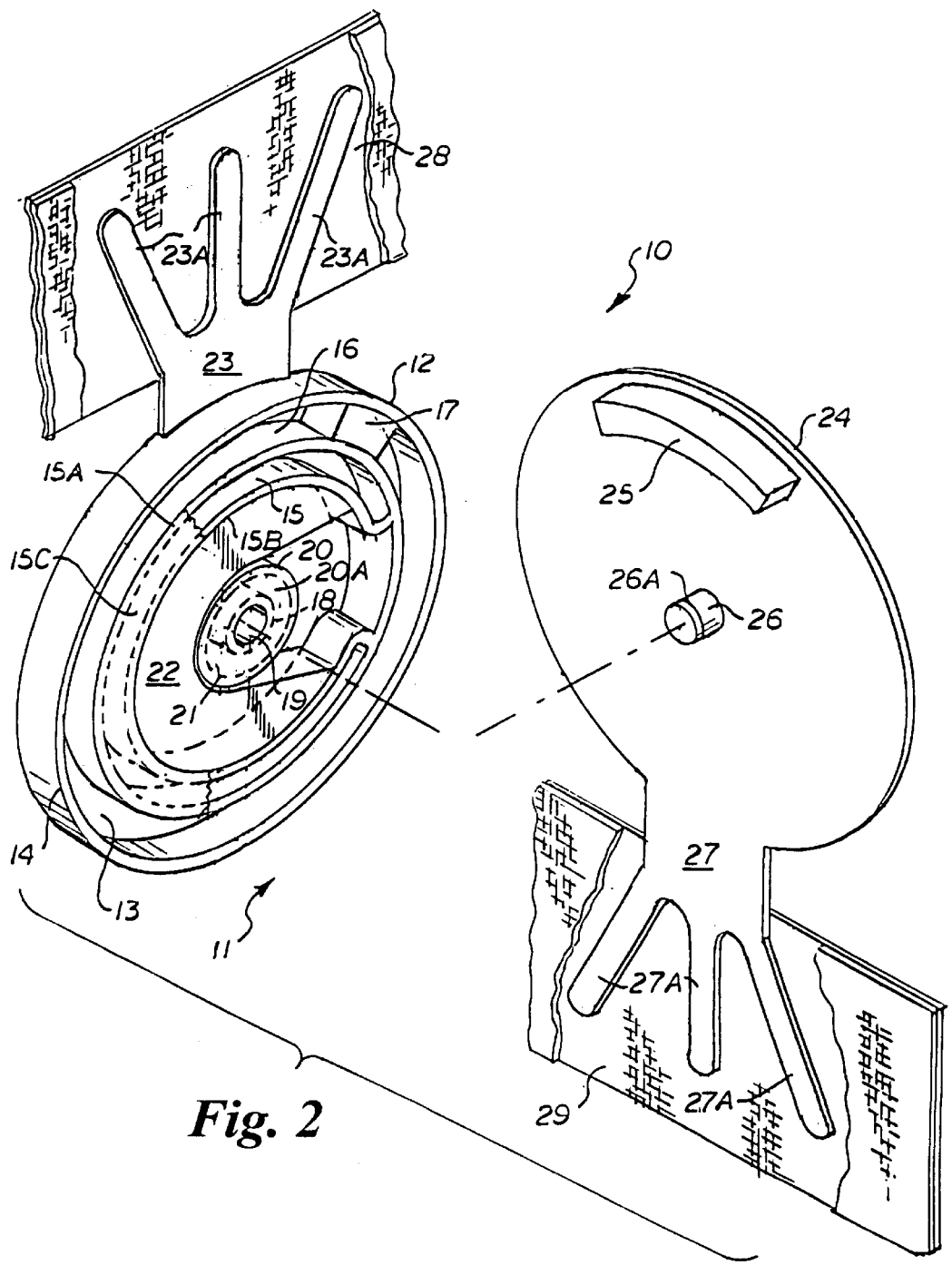
FIG. 2 is an exploded isometric view of the disk members of the hinge appliance, shown in an unassembled condition.

As shown in FIGS. 1 and 2, the diverging fingers 23A and 27A of the upper arms 23 and lower arms 27 are each secured to respective upper and lower fabric straps or bands 28 and 29. Each strap or band 28 and 29 is formed of an elastic material provided with VELCRO (tm) fastener s or other suitable material for securing it around the limb. The fingers 23A and 27A may be secured to the strap or band 28,29 by sewing them between two plies of the material, by gluing, or other conventional means. Preferably the straps or bands 28 and 29 are capable of slightly stretching along their x-axis but not along their y-axis. The inner facing surfaces of the hinge assembly which face the limb may also be provided with padding (not shown).

The straps or bands 28 and 29 are wrapped around the thigh and calf while the wearer is in a seated position with the knee joint bent at an angle of about 90°. The diverging fingers 23A,27A are of sufficient length and sufficiently flexible to partially encircle the limb. When properly positioned, the center of the hinge assemblies 11 are disposed on opposed lateral sides of the knee joint with their centers aligned along a transverse axis extending through the knee joint (FIG. 1).

As represented by dashed line in FIG. 1, after the hinge assemblies 11 are properly positioned and secured on the leg, a protective elastic stocking or sleeve 32 is pulled over the assembly. A commercially available elastic sleeve or elastic knee brace may be suitable for this use.

Referring again to FIG. 6, the hinge assembly 11 is shown in a rotating or pivot position during normal flexure of the knee joint. In the position shown, the kneecap of the wearer would be oriented toward the left-hand side of the figure. In this position as the knee joint flexes, the lower leg of the wearer moves relative to the upper leg, and the lower arm 27 of the second disk 24 moves relative to the upper arm 23 of the first disk 12, as indicated by arrow Al. During this action, the pin 26 rotates in the hub 18 and the cam 25 slides unrestricted in the channel 16, as indicated by the arrow A2.

Should a blow to the front to the knee occur, the cam 25 will rotate to the right and engage the stop member 17 to prevent further travel, and the upper and lower arms 23 and 27 would be in approximately vertical alignment at the stopping point. This reduces the likelihood of serious injury to the knee from a front impact.

Figure 7:
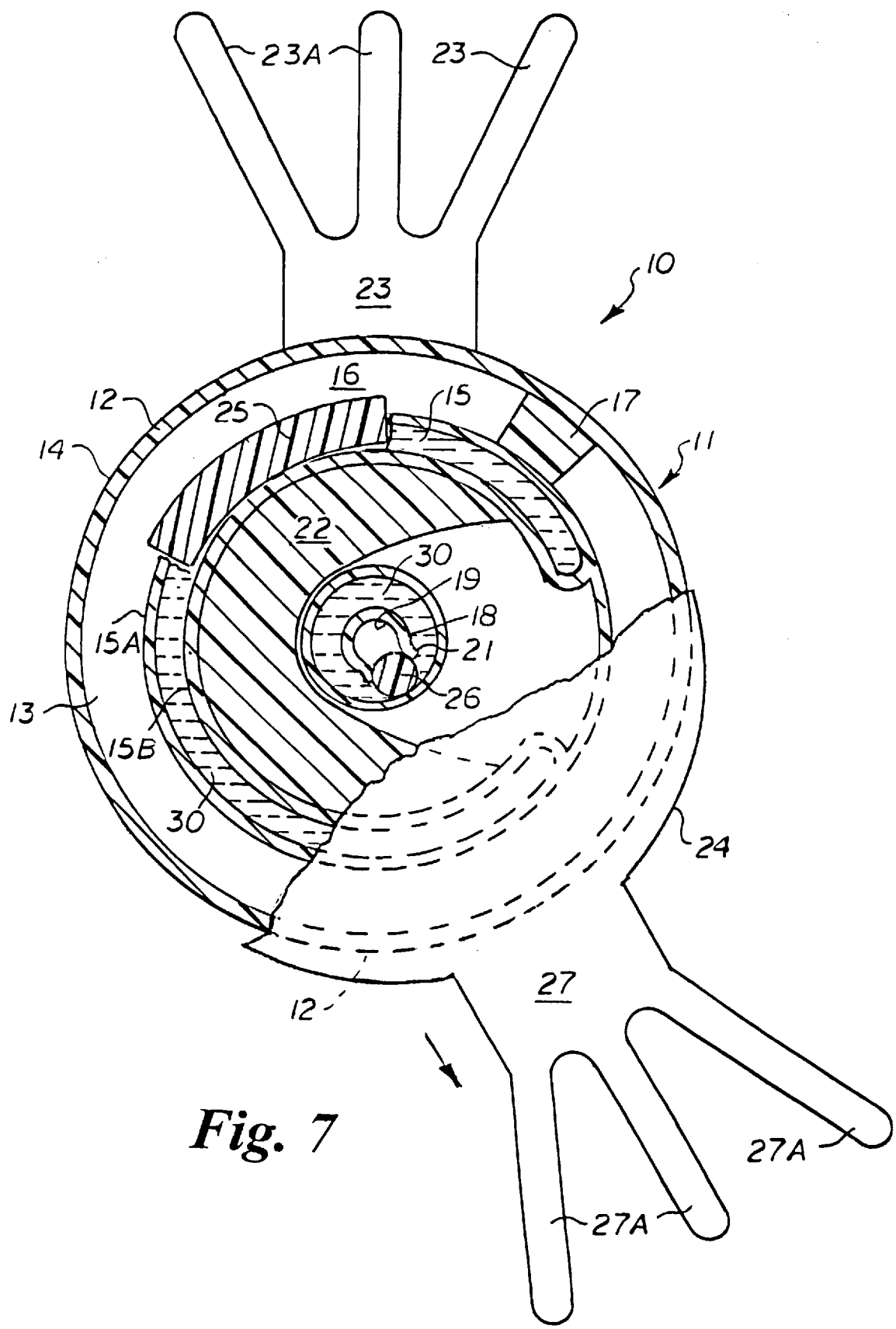
FIG. 7 is a transverse cross section through the assembled disk members, showing the cam and pin members in a position following a hard lateral impact.

As stated above, the enclosed chambers 15 and 21 are filled with a colored liquid 30 and the wall thickness of the outer wall 15A of the chamber 15 and the wall of the central hub 18 that receives the pin 26 are sufficiently thin or flexible so as to become distorted or may be frangible to break upon a predetermined sufficient force. As shown in FIG. 7, when the knee joint receives a side or lateral blow of sufficient predetermined force, the cam 25 forcefully engages the outer wall 15A of the chamber 15 and the pin 26 forcefully engages the wall of the central hub 18 causing the thin walls to become distorted or to break. As the walls become distorted or broken, further travel of the cam 25 is halted by the stop member 22 and further travel of the pin is halted by the outer wall 20 surrounding the hub to reduce the likelihood of serious injury to the knee from a lateral impact.

Distortion or breakage of the walls 15A of the chamber 15 and hub 18 releases the colored liquid 30 from the chambers 15 and 21 which will then leak out of the hinge assembly and become visible as it is absorbed by the lower strap or band 29 or on the protective sleeve 32 generating a means for visually indicating relative movement between the wearer's thigh and calf exceeding a predetermined amount. This visually indicates that the knee joint has received a serious lateral or frontal impact and warns the wearer, and also indicates that a replacement hinge assembly is needed.

While this invention has been described fully and completely with special emphasis upon a preferred embodiment, it should be understood that within the scope of the appended claims the invention may be practiced otherwise than as specifically described herein.

What is claimed is:

1. A knee hinge appliance to be worn on the leg of a user to supplement the natural resistance of the knee joint to excessive movement and prevent injury to the knee joint, comprising:

first and second pairs of first and second juxtaposed disk members adapted to lie on opposite sides of the wearer's knee joint, each of said first and second disk members secured together to rotate relative to one another about a transverse axis extending through the wearer's knee joint during use;

an upper arm extending generally vertically from each said first disk member to move therewith adapted to lie on opposite sides of the wearer's thigh;

a lower arm extending generally vertically from each said second disk member to move therewith adapted to lie on opposite sides of the wearer's calf;

an upper band associated with each said upper arm for encircling the wearer's thigh to secure and hold said upper arms thereon;

a lower band associated with each said lower arm for encircling the wearer's calf to secure and hold said lower arms thereon;

each said first disk member having a circular channel radially spaced from said transverse axis with stop member disposed therein, and each said second disk member having a cam element slidably received in said channel;

said cam element sliding freely in an arcuate path in said circular channel during normal flexion and extension of the wearer's leg while preventing excessive relative lateral movement between the wearer's thigh and calf, and said cam engaging said stop member to prevent rotation when the knee is subjected to a blow from the front and means for visually indicating relative movement between the wearer's thigh and calf exceeding a predetermined amount, said means for indicating relative movement contained between said first and second juxtaposed disk members.

2. The knee hinge appliance according to claim 1, wherein said means for visually indicating relative movement is carried by each pair of said first and second juxtaposed disk members for indicating that relative lateral movement between the wearer's thigh and calf exceeding a predetermined amount has occurred.

3. The knee hinge appliance according to claim 2, wherein said means for visually indicating relative movement comprises a colored liquid contained between said first and second juxtaposed disk members that is released upon relative lateral movement between said first and second disk members exceeding a predetermined amount.

4. The knee hinge appliance according to claim 1, wherein said means for visually indicating relative movement is carried by each pair of said first and second juxtaposed disk members for indicating that the wearer's knee joint has received a blow from the front exceeding a predetermined force.

5. The knee hinge appliance according to claim 4, wherein said means for visually indicating relative movement comprises a colored liquid contained between said first and second juxtaposed disk members that is released upon relative movement between said first and second disk members caused by the wearer's knee receiving a blow from the front exceeding a predetermined force.

6. The knee hinge appliance according to claim 1, further comprising:

an outer removable protective elastic sleeve substantially encircling said first and second pairs of said first and second juxtaposed disk members, said upper and lower arm, and said upper and lower bands.

7. The knee hinge appliance according to claim 1, wherein each said first disk member is a first circular disk having a flat end wall, a circumferential side wall, and a generally C-shaped chamber spaced radially inward from said circumferential side wall;

said C-shaped chamber having a circular outer wall and a concentric inwardly spaced C-shaped inner wall adjoined thereto by a top wall that encloses said C-shaped chamber;

said chamber circular outer wall spaced radially inward from said first disk circumferential wall defining said circular channel that receives said second disk cam element;

said stop member is secured in said channel in circumferentially offset relation to a vertical axis extending through a center of said upper arm;

each said second disk member is a generally flat circular disk; and said cam element is an arcuate cam element protruding from said second disk member flat surface and slidably received in said first disk member circular channel.

8. The knee hinge appliance according to claim 7, wherein each said first disk member has a central tubular hub with an inwardly extending central bore, a circular outer wall encircling said central hub in concentric radially spaced relation and adjoined thereto by a top wall to form a second enclosed chamber surrounding said central hub;

a generally C-shaped second stop member partially encircling said outer wall encircling said central hub; and each said second disk member has a central cylindrical pin protruding from said flat surface and rotatably received in said central bore of said hub of said first disk member.

9. The knee hinge appliance according to claim 8, wherein said central bore has a circumferential groove at its bottom end;

said cylindrical pin has a circumferential raised bead at its outer end that is snapped into sliding engagement in said groove to secure said first and second disk member together to rotate relative to one another.

10. The knee hinge appliance according to claim 8, wherein each said upper and lower arm comprises a thin flat member having flat diverging fingers at an outer end, and each said upper and lower band is secured to said diverging fingers of said upper and lower arms, respectively.

11. The knee hinge appliance according to claim 8, wherein said enclosed C-shaped chamber and said second enclosed chamber each contain a liquid to absorb shock during relative lateral movement between said first and second disk members.

12. The knee hinge appliance according to claim 8, wherein said enclosed C-shaped chamber and said second enclosed chamber each contain a colored liquid; and said outer wall of said C-shaped chamber and said tubular hub are sufficiently flexible to become distorted upon the wearer's knee receiving an impact from the front or side exceeding a predetermined force to release said colored liquid indicating that the wearer's knee has received a blow from the front or side exceeding a predetermined force.

13. The knee hinge appliance according to claim 8, wherein said enclosed C-shaped chamber and said second enclosed chamber each contain a colored liquid; and said outer wall of said C-shaped chamber and said tubular hub are sufficiently frangible to become ruptured upon the wearer's knee receiving an impact from the front or side exceeding a predetermined force to release said colored liquid indicating that the wearer's knee has received a blow from the front or side exceeding a predetermined force.

* * * * *